(12) United States Patent
Klaassen et al.

(10) Patent No.: US 9,616,148 B2
(45) Date of Patent: Apr. 11, 2017

(54) METHOD AND DEVICE FOR DISINFECTING A SPACE

(75) Inventors: Frank Olaf Klaassen, Kortenhoef (NL); Sander Albert Alma, Kortenhoef (NL); Carolus Borromeus H. Musters, Laren (NL); Paul Plantinga, Huizen (NL); Cornelis Pieter Timmerman, Utrecht (NL)

(73) Assignee: Infection Control B.V., Eemnes (NL)

( * ) Notice: Subject to any disclaimer, the term of this patent is extended or adjusted under 35 U.S.C. 154(b) by 2457 days.

(21) Appl. No.: 12/294,783

(22) PCT Filed: Apr. 27, 2007

(86) PCT No.: PCT/EP2007/054157
§ 371 (c)(1),
(2), (4) Date: May 17, 2010

(87) PCT Pub. No.: WO2007/125100
PCT Pub. Date: Nov. 8, 2007

(65) Prior Publication Data
US 2010/0233020 A1    Sep. 16, 2010

(30) Foreign Application Priority Data

Apr. 28, 2006  (NL) ...................................... 2000064

(51) Int. Cl.
*A61L 2/22* (2006.01)
*A61L 2/20* (2006.01)
(Continued)

(52) U.S. Cl.
CPC ................ *A61L 2/208* (2013.01); *A61L 2/22* (2013.01); *A61L 2/24* (2013.01); *A61L 9/015* (2013.01);
(Continued)

(58) Field of Classification Search
CPC ...................................................... A61L 2/025
(Continued)

(56) References Cited

U.S. PATENT DOCUMENTS 5,173,258 A     12/1992 Childers
2003/0143110 A1  7/2003 Kritzler et al.
(Continued)

FOREIGN PATENT DOCUMENTS

DE     10234768 A1    12/2004
EP      0774263 A1    5/1997
(Continued)

OTHER PUBLICATIONS

Gorenstein, "Ultrasonic Aerolization" Technology, Announcement Green Clouds Ltd., Jan. 1, 1996, 8 pages.
(Continued)

*Primary Examiner* — Sean E Conley
(74) *Attorney, Agent, or Firm* — Bret E. Field; Bozicevic, Field & Francis LLP (57) ABSTRACT

The present invention relates to a method and device for disinfecting a space and the objects present therein, wherein the method comprises at least the following steps of: (a) determining a first value of the relative humidity of the air in the space; (b) vaporizing a disinfecting liquid in the space until a predetermined second value of the relative humidity of the air in the space is reached; and (c) maintaining the relative humidity of the air at the second value for a predetermined time by means of vaporizing the disinfecting liquid, wherein the vaporization of the disinfecting liquid takes place by means of ultrasonic sound waves. With the method and device according to the invention all kinds of spaces of differing dimensions can be disinfected in very effective manner.

13 Claims, 3 Drawing Sheets

(51) Int. Cl.
*A61L 2/24* (2006.01)
*A61L 9/015* (2006.01)
*A61L 9/14* (2006.01)

(52) U.S. Cl.
CPC .............. *A61L 9/14* (2013.01); *A61L 2202/16* (2013.01); *A61L 2202/25* (2013.01)

(58) Field of Classification Search
USPC .......................................................... 422/20
See application file for complete search history.

(56) References Cited

U.S. PATENT DOCUMENTS

| | | | |
|---|---|---|---|
| 2004/0005240 A1* | 1/2004 | Adiga et al. ...................... | 422/1 |
| 2004/0009094 A1 | 1/2004 | Adiga et al. | |
| 2005/0019206 A1* | 1/2005 | Centanni ........................... | 422/3 |
| 2005/0284822 A1 | 12/2005 | Yehuda et al. | |
| 2008/0289971 A1* | 11/2008 | Shigihara et al. ............ | 205/687 |

FOREIGN PATENT DOCUMENTS

| | | |
|---|---|---|
| EP | 1226834 A1 | 7/2002 |
| EP | 1500404 | 1/2005 |
| EP | 1759715 A1 | 3/2007 |
| GB | 2165948 A | 4/1986 |
| GB | 2331810 A | 6/1999 |
| WO | WO2005014054 A2 | 2/2005 |
| WO | WO2007125100 A1 | 11/2007 |

OTHER PUBLICATIONS

Gustin et al., Facility decontamination of anthrax spores utilizing vaporized hydrogen Peroxide (VHP), Feb. 11, 2010, 2 pages.
Krause et al., Biodecontamination of animal rooms and heat-sensitive equipment with vaporized hydrogen peroxide, Contemp Top Lab Anim Sci. Nov. 2001; 40(6):18-21.
Stennis, Report of beta test with Stennis Desinfection technology, Gooi Noord Ziekenhuis, Department of Medical Microbilogy, Sep. 1, 2004, 6 pages.
Stennis, Report from Infectionhygenic section, Feb. 2005, 5 pages.
Mitchell, Are ambulances and patient transport services delivering more than patients to and from hospitals?, Steris Limited and Femo, UK, Apr. 6, 2005, 4 pages.
Tackney, The Validation of the Sterinis Machine at Adelaide Meath Hospital, Tallaght, Dublin, BA (Mod) Thesis 2005, 21 pages.
Trench et al., Tackling contamination of the hospital environment by methicillin-resistant Staphylococcus aureus (MRSA): a comparison between conventional terminal cleaning and hydrogen peroxide vapour decontamination, J Hosp Infect. May 2004; 57(1):31-7.

* cited by examiner

METHOD AND DEVICE FOR DISINFECTING A SPACE

The present invention relates to a method and device for disinfecting a space and the objects possibly present therein.

In, among others, the food, pharmaceutical, biotechnological and medical industries, as well as in health care institutions and in the agrarian sector the disinfection of spaces, such as for instance surgical wards, and the objects therein, such as for instance medical equipment, is generally known and of very great importance. Through the disinfection of such spaces, such as for instance operating rooms and nursing wards, the number of micro-organisms (such as bacteria, viruses, fungi) in the space and on the objects therein is greatly reduced. In this way nosocomial infections of patients and/or staff in hospitals can for instance be combated and prevented.

The traditional disinfection methods for such spaces consist, among others, of manual cleaning of surfaces using chemical disinfectants. When the surfaces are wiped clean however, only the relevant surface which can be reached by hand is treated, and not for instance the air and locations in this space which cannot be reached by hand. Furthermore, staff is necessary for the purpose of cleaning and the effectiveness of the cleaning depends, among other factors, on the person carrying out the cleaning, which thus does not always lead to the same results.

It is also known to make use of special spray devices with which a disinfecting liquid is sprayed into the space and onto the objects present therein. The known spray devices produce liquid droplets with a size of more than 20 μm, in general even between 80 and 200 μm (usually by atomization under pressure from a nozzle). Due to the size and density of these droplets a so-called "umbrella effect" will occur during spraying, wherein a high concentration of the disinfecting liquid remains close to the spray device and the amount of disinfectant in the air decreases very rapidly as the distance from the spray device increases. In this manner the space and the objects present therein will not be disinfected uniformly because the disinfecting liquid will not reach some locations, or hardly so (see FIG. 1).

Despite the existing disinfection methods it occurs more and more frequently that during a stay in hospital patients are infected with pathogenic hospital bacteria, such as among others the antibiotic-resistant MRSA bacteria.

The object of the invention is to provide a method and device for effectively disinfecting spaces and the objects possibly present therein.

This objective is achieved by the invention in that the method comprises at least the following steps of:

(a) determining a first value of the relative humidity (RH) of the air in the space;

(b) vaporizing a disinfecting liquid in the space until a predetermined second value of the relative humidity of the air in the space is reached; and (c) maintaining the relative air humidity at the second value for a predetermined time by means of vaporizing the disinfecting liquid, wherein the vaporizing of the disinfecting liquid takes place by means of ultrasonic sound waves.

With the method according to the invention the spaces and the objects possibly present therein are disinfected effectively. Indeed, even an optimal reduction (>log 5) of the micro-organisms may be achieved.

In a preferred embodiment of the invention vaporization of the disinfecting liquid takes place by means of ultrasonic sound waves at a frequency from 1.5 MHZ to 2.8 MHz, preferably at a frequency from 1.5 MHz to 2.0 MHz, for example at a frequency of about 1.7 MHZ. Used for this purpose are ultrasonic elements, so-called piezoelectric ceramic discs. These ultrasonic elements are situated in the disinfecting liquid and are driven using an ultrasonic generator which sends current pulses to the elements at a frequency of for instance 1.7 MHZ (1,700,000 vibrations per second). These current pulses cause the elements in the same frequency to expand and contract, whereby they are set into vibration and the disinfecting liquid in which the elements are arranged also begins to vibrate. Because the disinfecting liquid is too slow to follow the movement of the ultrasonic elements, small vacuum bubbles are created in the liquid. These bubbles then implode under the influence of the surface tension of the liquid, a phenomenon known as cavitation. Very great forces can occur, whereby the liquid is pushed out of the liquid surface in the form of very small droplets. These small droplets are then taken up into the air being guided over the bath with disinfecting liquid. Due to the small dimensions and weight of the liquid droplets no condensation occurs.

According to a preferred embodiment of the method, a first value of the relative humidity (RH) of the air in the space, i.e. the initial value, is first determined. The disinfection cycle is then started after a predetermined time. Any personnel that may be present must all leave the space before vaporization of the disinfecting liquid begins. When the disinfection cycle begins the disinfecting liquid is vaporized until a predetermined second value of the relative humidity in the space is reached, whereafter this RH is maintained at this value for a predetermined time by means of vaporizing the disinfecting liquid. After said predetermined period of time has ended, the ultrasonic generator is switched off and no more disinfecting liquid is vaporized. It is subsequently possible to enter the space again after a predetermined period of time.

In a preferred embodiment of the invention the second value of the relative humidity is higher than the initial value measured in step (a). The second value of the relative humidity is preferably at least 10% higher, more preferably at least 15%, more preferably at least 20% higher than the first value. In a particular preferred embodiment of the invention the second value of the relative humidity is at least 25% higher, preferably even up to 40% or more, than the initial value. Increasing the relative humidity in the space by atomizing the disinfecting liquid achieves that the produced mist with the disinfectant dissolved therein is taken up into the air that is present. Because the air humidity is the same in the whole space (homogeneous distribution), the vaporized disinfectant will also spread homogeneously in the space. The increase in the RH is directly proportional to the amount of disinfectant in the air. Because air with a lower RH readily absorbs moisture, the produced mist will move to these locations. This means that the vaporized liquid, and thus the disinfectant, reaches every nook and cranny of a space (natural diffusion process). By maintaining the level of the RH for a determined period (generally between for instance 30 and 300 minutes, e.g. about 90 minutes) there is more than sufficient contact time between the disinfectant and the micro-organisms to eliminate these latter (decontamination process).

In the context of the present invention, micro-organisms are understood to mean for instance bacteria, spores, fungi, viruses and mites. The method of the present invention is in particular effective in eliminating one or more of the micro-organisms selected from the group consisting of *Staphylococcus aureus*, MRSA, *Enterococcus faecalis, Acinetobacter baumanni, Pseudomonas aeruginosa, Bacillus*

*subtilis, Bacillus stearothermophilus, Aspergillus niger, Candida albicans, Enterococcus hirae, Mycobacterium terrae, Mycobacterium avium,* and *Dermatophagoides pteronyssinus.*

The disinfecting liquid, which is vaporized according to the method, preferably comprises hydrogen peroxide as disinfectant. Hydrogen peroxide is normally mixed with water and has very good disinfecting properties. It is known that the cell membranes of the micro-organisms burst open due to the oxidizing action of hydrogen peroxide. Hydrogen peroxide moreover has the advantage of breaking down into water and oxygen, and no toxic residues therefore remain. With the method of the present invention low concentrations of hydroxide peroxide can be used. Thus, a 5% solution of hydrogen peroxide in vaporized form, although causing slight irritation to the mucous membranes in some cases, is completely non-hazardous in contact with humans. According to the present invention, such hydrogen peroxide in vaporized form has surprisingly been shown to be very effective, even using low concentrations, in disinfecting spaces and the objects present therein.

In a particular embodiment the disinfecting liquid comprises a combination of hydrogen peroxide and silver ions. The silver ions may be present in a concentration of about 50 ppm, but may also be present in higher concentrations, for example up to 500 ppm or even more. A synergistic decontaminating effect is achieved by combining these constituents. All pathogenic bacteria, as well as the spores of for instance *C. difficile,* also the antibiotic-resistant MRSA bacteria, *Acinetobacter,* and viruses such as HIV, norovirus and influenza virus and fungi can, among others, be eliminated.

Using the method according to the invention, and particularly when a combination of hydrogen peroxide and silver ions is used, lower concentrations of hydrogen peroxide can be used than is usual with the existing disinfection methods. The concentration of hydrogen peroxide in the disinfecting liquid thus preferably lies between 1-30 vol. %, more preferably between 1-10 vol. %, and most preferably is about 5 vol. %. This concentration gives an excellent decontaminating effect, while harmfulness and toxicity are negligible. With moderate ventilation of the space after vaporization, the residue that is present is already less than $\frac{1}{10}$ of the permitted MAC (maximum acceptable concentration) value after about one hour. The MAC of a gas, vapour, mist or substance is that concentration in the air which, as far as present knowledge extends, generally does not adversely affect the health of employees or their progeny in the case of repeated exposure of an employee for a longer period or even for their working life. This applies under the following conditions:

1. for healthy adult persons;
2. for eight-hour working periods interrupted by breaks in a non-contaminated atmosphere;
3. for a working week of a maximum of 40 hours;
4. in the case of work which is physically not too heavy;
5. extra protection is available in the case of substances easily absorbed via the skin;
6. absence of other toxic substances in the workspace.

The list of MAC values forms part of schedule 3 of the policy guidelines of the Working Conditions Act in the Netherlands.

With the method according to the invention the disinfecting liquid is preferably vaporized to a droplet size smaller than 10 µm, more preferably smaller than 5 µm and most preferably to a droplet size smaller than 3 µm, such as about 1 µm. Because these very small droplets are easily taken up into the air, the disinfecting liquid is distributed very uniformly through the space and in this way reaches all surfaces of the objects possibly present in the space. It is moreover guaranteed that the disinfecting liquid together with the air reaches locations which cannot be reached with the existing disinfection techniques, such as within equipment for example. Due to the very small droplets condensation occurs only at the saturation point.

The method according to the invention is particularly suitable for use in rooms and spaces in the medical and pharmaceutical world, such as for instance for the purpose of treating and disinfecting spaces and materials in hospitals. The method can however also be used for diverse other applications where it is desirable to reduce the number of microorganisms, such as for instance for the purpose of disinfecting sheds in the poultry and cattle-farming sector, but also in the food industry as well as saunas and swimming pools.

The invention also relates to a device for performing the above described method.

The invention particularly relates to a device for disinfecting a space and the objects possibly present therein, which device at least comprises:

(a) means for determining the relative humidity of the air in the space;

(b) means for vaporizing a disinfecting liquid in the space using ultrasonic sound waves; and (c) means for monitoring and maintaining a predetermined relative humidity of the air in the space.

With the device according to the invention spaces of different dimensions, such as operating rooms but also ambulances etc., can be disinfected in very suitable manner.

In a preferred embodiment of the invention the device further comprises means for supplying and guiding air from the space along the disinfecting liquid.

In a particular embodiment the device further comprises indicator means for indicating the status of the device, i.e. whether the device is switched on or off. The presence of these indicator means increases safety, since it is possible to indicate when the device is switched on and disinfecting liquid is being vaporized, and no staff should therefore be present in the space. The indicator means can for instance comprise visual indicator means (such as a (coloured) lamp), auditory indicator means (such as a sound signal, or a combination thereof.

The ultrasonic means for vaporizing the disinfecting liquid preferably comprise one or more ultrasonic elements (in particular ceramic discs) which are driven by means of an ultrasonic generator, which preferably generates ultrasonic generator sound waves with a frequency of at least 1.5 MHZ, more preferably a frequency of about 1.7 MHZ.

The device further may comprise a container for the disinfecting liquid to be vaporized. The ultrasonic elements are preferably arranged in the disinfecting liquid so that the ultrasonic vibrations are transmitted directly to the disinfecting liquid.

After measurement of the initial value of the RH in the air the vaporization is started by switching on the ultrasonic generator which drives the ultrasonic elements as described above. As soon as a predetermined value of the RH in the air is reached, for instance a value which is 25% higher than the initial value, this RH will be maintained at this value for a determined time, for instance about 90 minutes. The ultrasonic generator will then be switched off. As long as the device is in operation, this can be indicated using indicator means, such as for instance a lamp, so that it is apparent that no staff may enter the space.

Once a disinfecting process has been carried out, the disinfecting liquid is preferably pumped back into a storage container in order to enhance safety and prevent liquid contamination.

The present invention thus provides a method and device which are able to generate an optimal disinfection level, even larger than log 5 for all kinds of rooms and spaces having smaller and bigger volumes, even up to 1000 m$^3$.

The invention is further illustrated with reference to the following, non-limiting, Examples and Figures.

Figure 1:
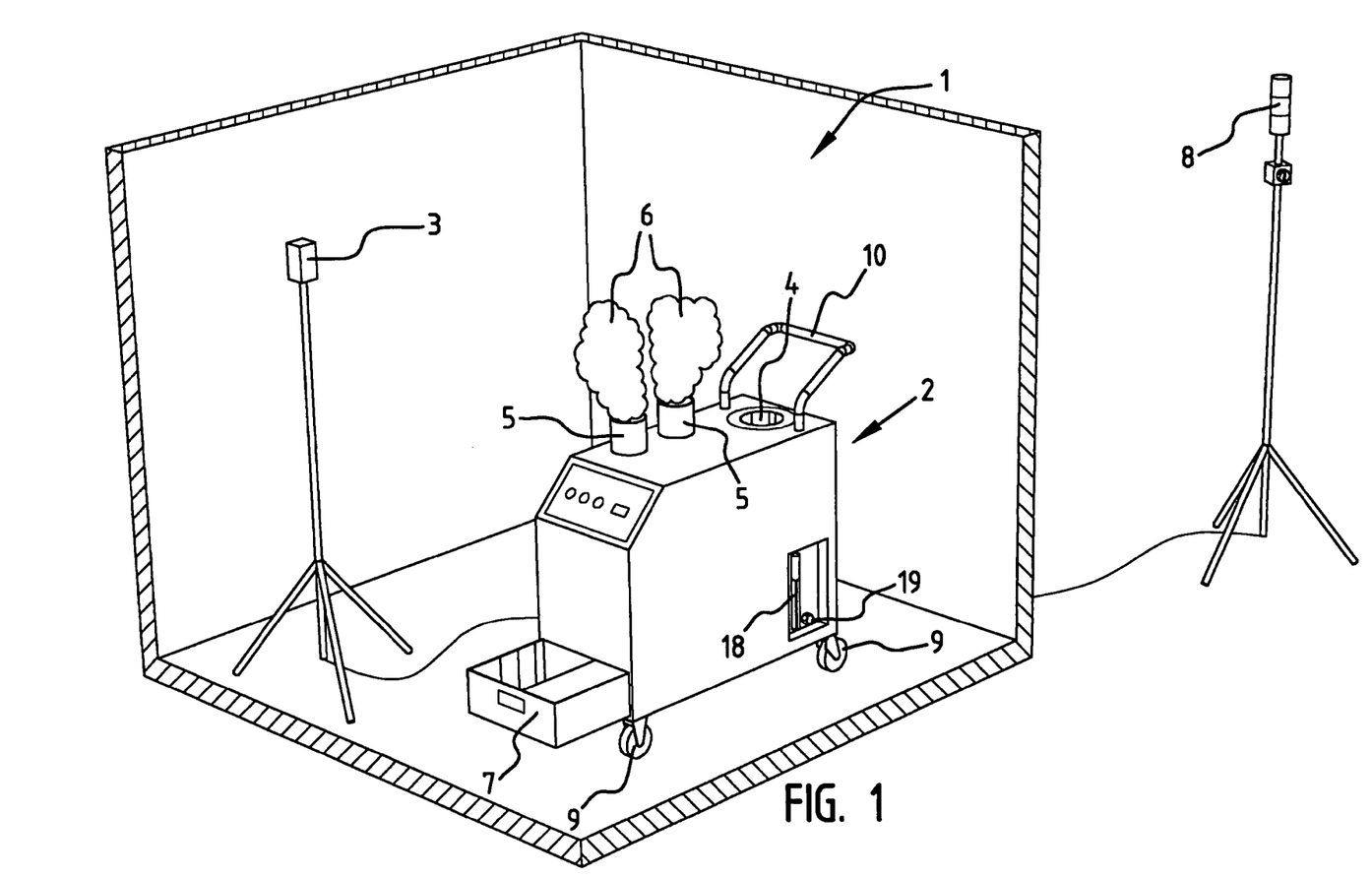
FIG. 1 shows a preferred embodiment of the device according to the invention in a space to be disinfected.

As shown in the embodiment of FIG. 1, a space 1, for instance an operating room, is disinfected with the vaporizing device 2 according to the invention. Vaporizing device 2 comprises a sensor 3 for measuring the relative humidity of the air in the space, which is coupled to device 2. It will be appreciated that the coupling between device 2 and sensor 3 can also take place wirelessly, for instance using Bluetooth. As described above, for the purpose of disinfecting the space a first value (initial value) of the relative humidity (RH) of the air in the space is first measured using sensor 3. A disinfecting liquid is subsequently vaporized in the space until a predetermined second value of the relative humidity of the air in the space is reached. This predetermined RH is preferably at least 25% higher than the initial value. This RH is maintained for a predetermined time (preferably at least 90 minutes) by means of vaporizing the disinfecting liquid. Vaporization of the disinfecting liquid takes place by means of ultrasonic sound waves as set forth below.

As shown further in FIG. 1, vaporizing device 2 comprises an inlet 4 for introducing a container with the disinfecting liquid to be vaporized. The device comprises two outlets 5 for the vaporized disinfecting liquid 6. In the embodiment shown in FIG. 1, device 2 further comprises a storage drawer 7 in which for instance loose components such as sensor 3 for measuring the RH can be stored. Device 2 further comprises indicator means consisting of one or more lamps 8 with which it is possible to indicate whether the device is switched on or off. Sensor 3 and lamps 8 are arranged on a stand. Indicator means 8 are connected to the device (this is optionally also possible via a wireless connection), and are preferably placed at a distance from device 2 and more preferably outside the space 1 to be disinfected, so that it is possible to see outside the space whether the device is switched on and disinfecting liquid is being vaporized. The vaporizing device as shown in FIG. 1 is easy to displace to another space for disinfecting due to the presence of wheels 9 and handle 10.

Figure 2:
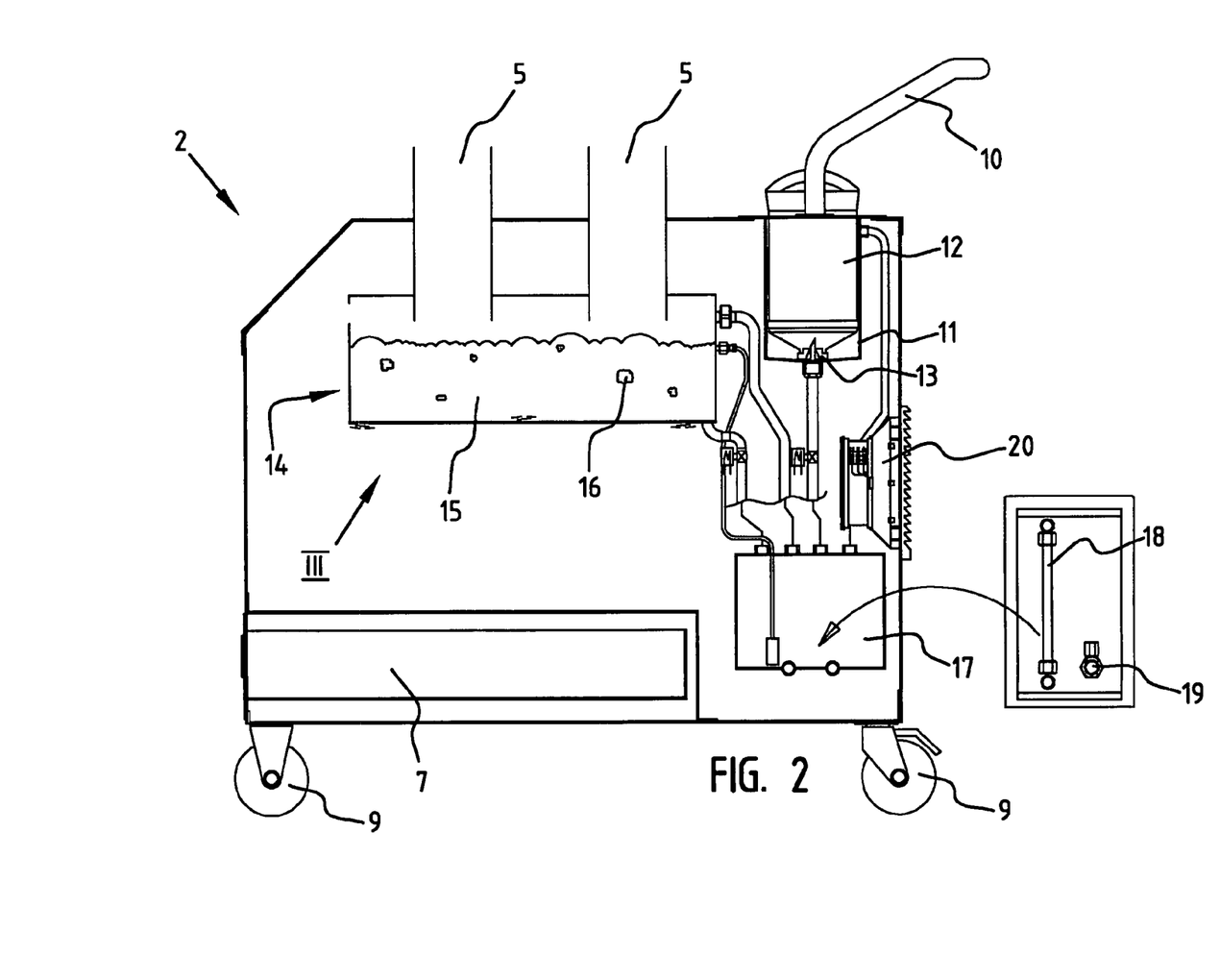
FIG. 2 shows a cross-section of the embodiment of FIG. 1.

As shown in the cross-section of FIG. 2, device 2 comprises in a preferred embodiment a holder 11 for receiving a container 12 with disinfecting liquid. Container 12 is arranged in holder 11 with the filling opening downward and pressed well down until filling pipe 13 protrudes through the closure, for instance a rubber cap, of the container. Storage tank 17 and vaporization unit 14 are then filled with disinfecting liquid 15. When storage tank 17 and vaporization unit 14 are filled with a minimum required quantity of disinfecting liquid 15, device 2 is ready for use. Vaporization unit 14 is in liquid communication with a storage tank 17. A gauge glass 18 on the outside of the device indicates the amount of disinfecting liquid in storage tank 17.

Figure 3:
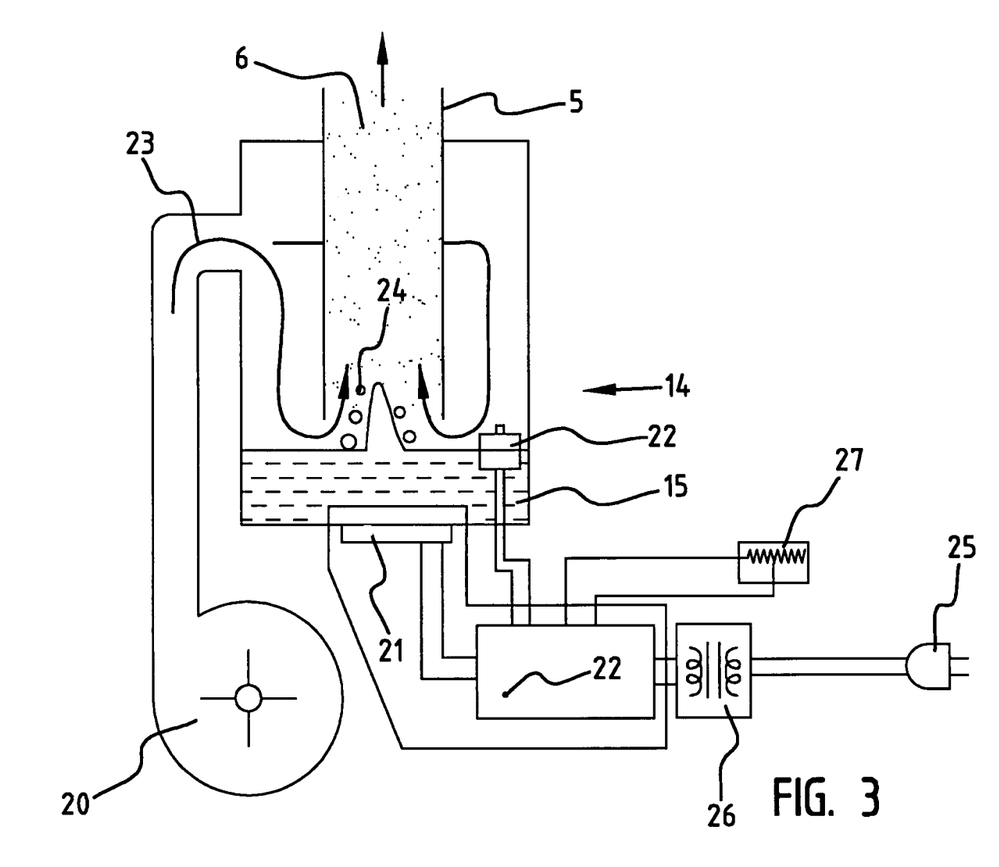
FIG. 3 shows schematically a vaporization unit, designated with III in FIG. 2.

Once the initial value of the relative humidity of the air in the space has been determined and optionally also the temperature in the space, the disinfecting liquid 15 in vaporization unit 14 is set into vibration using ceramic elements as shown in FIG. 3.

FIG. 3 shows vaporization unit 14 schematically. Ceramic element 21 is set into vibration using ultrasonic generator 22. FIG. 3 shows one ceramic element 21. The device preferably comprises a plurality of ceramic elements. Ultrasonic element 21 is in direct contact with the disinfecting liquid 15. In the shown embodiment a liquid column of preferably between 35 and 40 mm is present above ultrasonic element 21. This liquid level is monitored using level switch 22. The ultrasonic elements can break down if there is no liquid thereon.

The vibration of the ultrasonic elements creates small vacuum bubbles 16 in liquid 15 (see FIG. 2). These bubbles 16 subsequently implode under the influence of the surface tension of the liquid, wherein very great forces can occur, whereby the liquid is pushed out of the liquid surface in the form of very small droplets 24 (FIG. 3). These small droplets are then taken up into the air and guided via outlet 5 into the space.

As shown in FIG. 3, device 2 comprises a fan 20 with which air 23 is drawn out of the space into atomizing device 2 and guided through atomizing unit 14 along the surface of disinfecting liquid 15, and is then discharged via outlet pipe 5. A part of the indrawn air is preferably also blown directly to the outside through an opening around the outlet pipe. This gives a venturi effect, whereby the mist does not linger in device 2 but is, as it were, drawn out of outlet pipes 5.

The device is for instance connected to the mains electricity using plug 25. Device 2 further comprises other components such as transformer 26 and control means 27 for regulating the mist formation.

As further shown in FIG. 2, the device can optionally also comprise a discharge 19 for emptying storage tank 17 if desired, for instance for servicing of the device. It is not necessary however to empty the storage tank after each use.

The efficacy of the method and device according to the invention are demonstrated in the following examples.

EXAMPLES

Example 1

Test Results Using the Disinfection Method and Device in a Regional Hospital in the Netherlands As indicated above, the method of the invention provides a new and highly effective ultra mist disinfection method for disinfection of for instance medical devices, rooms, and surfaces.

The method and device of the invention have been tested in a regional hospital in the Netherlands. The hospital comprises 456 beds and has most medical specialties available.

Materials and Methods

The test was performed on five microorganisms, in particular: *Staphylococcus aureus*, MRSA, *Enterococcus faecealis, Acinetobacter baumanni*, and *Pseudomonas aeruginosa*.

The disinfectant agent used consisted of 5 vol-% hydrogen peroxide and 50 ppm silver in water.

The five types of bacteria were used to be put on 3 different test locations in a normal sized, 1 bed patient room with adjacent bathroom (total volume about 75 m$^3$). The three test locations comprised the window of the patient room, a table in the patient room and the bathroom.

These three test locations were contaminated with the microorganisms using suspensions of the microorganisms with a density of 2 Mac Farland (24 hours cultures on blood agar) (>$10^5$ cfu/ml). The suspensions with the microorganisms were dispersed on the test surfaces, each of about 10 cm$^2$. Each location had double control areas, i.e. a double sample taken from each area before beginning the vaporization (T1), a double sample taken after vaporization of the disinfectant using the method of the present invention (T2), and a double sample taken 4 hours after stopping the method of the invention (T3). This test was performed for all 5 microorganisms and contaminated locations.

Previously, the room has been prepared and thoroughly cleaned according to standard hospital protocol. To eliminate any air flux in the room all air conducts of the central hospital air condition were closed with plastic and tape.

Subsequently, the device according to the invention was placed in a corner of the room and run in order to disinfect the room.

Table 1 shows the test parameters, such as time, temperature, and relative humidity before and during the method. The disinfecting liquid was vaporized to an average droplet size of 2 μm. The frequency of the ultrasonic sound waves used was 1.7 MHz.

TABLE 1

| Description | Time | Temp (° C.) | RH (%) |
| --- | --- | --- | --- |
| Start process (T1) | 18:40 | 26.8 | 52.4 |
| System ready (vaporization stopped) | 20:10 | 26.5 | 80 |
| Room safe (green light) (T2) | 20:40 | 26.4 | 78 |
| T3 | 0:00 | 26 | 60 |

Results

The test results for each of the locations have been summarized in Table 2 (location 1: window patient room), Table 3 (location 2; table patient room) and Table 4 (location 3: bathroom).

TABLE 2

| | Location 1 | | | | | |
| --- | --- | --- | --- | --- | --- | --- |
| | Control on T1 | | T2 | | T3 | |
| Test results | S1 | S2 | S1 | S2 | S1 | S2 |
| Staphylococcus aureus | + | + | − | − | − | − |
| MRSA | + | + | − | − | − | − |
| Entererococcus faecalis | + | + | − | − | − | − |
| Acinetobacter baumanni | + | + | − | − | − | − |
| Pseudomonas aeruginosa | − | + | − | − | − | − |

TABLE 3

| | Location 2 | | | | | |
| --- | --- | --- | --- | --- | --- | --- |
| | Control on T1 | | T2 | | T3 | |
| Test results | S1 | S2 | S1 | S2 | S1 | S2 |
| Staphylococcus aureus | + | + | − | − | − | − |
| MRSA | + | + | − | − | − | − |
| Entererococcus faecalis | + | + | − | − | − | − |
| Acinetobacter baumanni | + | + | − | − | − | − |
| Pseudomonas aeruginosa | + | + | − | − | − | − |

TABLE 4

| | Location 3 | | | | | |
| --- | --- | --- | --- | --- | --- | --- |
| | Control on T1 | | T2 | | T3 | |
| Test results | S1 | S2 | S1 | S2 | S1 | S2 |
| Staphylococcus aureus | + | + | − | − | − | − |
| MRSA | + | + | − | − | − | − |
| Entererococcus faecalis | + | + | − | − | − | − |
| Acinetobacter baumanni | + | + | − | − | − | − |
| Pseudomonas aeruginosa | + | + | − | − | − | − |

In Table 2, 3 and 4:
S1=test sample 1
S2=test sample 2
+: microorganisms present
−: no microorganisms present Conclusions The validation tests with the method and device according to the present invention in a hospital environment have shown that the method and device are very effective against at least *Staphylococcus aureus*, MRSA, *Enterococcus faecealis, Acinetobacter baumanni*, and *Pseudomonas aeruginosa*, which are microorganisms that are commonly present in hospitals and may be the cause of serious nosocomial infections. Thus, it has been demonstrated that homogeneous volume surface log 5 reductions can be obtained easily. In addition, the method of the invention has been shown to be reproducible and to be easy to use for the hospital personnel. Due to the effective safety measures the disinfection procedure is 100% safe for all hospital personnel.

Example 2

Results of Tests Based on the European Suspension Test (EST)

The European Suspension test is a known, standardized test which generally is used for testing the efficacy of disinfectants and antiseptics (European Committee for Standardization CEN/TC 216 Workgroup 1-4). According to this test, disinfectants are contacted, for a period of 5 minutes, with suspensions comprising known amounts of five different micro-organisms having different properties, i.e. a gram-positive bacteria, a gram-negative bacteria, a spore-forming bacteria, a yeast or fungus, and a Pseudomonas bacteria, in order to obtain at least a log 5 reduction (log/cfu) in the amount of bacteria.

The amount of microorganisms present on the location after disinfecting is determined and compared with a control (the same amount of micro-organisms, no disinfectant used). In the case where, for example, the amount of microorganisms present at the control (i.e. location not treated with disinfectant) is e.g. $10^7$, and wherein the amount of microorganisms on the test location (i.e. after treatment with disinfectant) is e.g. $10^1$, the microbicide effect (log/cfu) is log $10^7$–log $10^1$=6.

A variant of the European Suspension Test has been performed using the disinfecting method and device according to the present invention. To this end, several locations were contaminated with varying concentrations of two types of microorganisms, *Bacillus subtilis* and *Bacillus stearothermophilus*.

Using the device according to the present invention, the first value of the relative humidity (RH) was determined to be 35%. By vaporizing the disinfectant the relative humidity was increased to 75%, which value was maintained during 120 minutes by vaporizing the disinfectant (comprising 5% hydrogen peroxide and 50 ppm silver in water). The disinfecting liquid was vaporized to an average droplet size of 2 μm. The frequency of the ultrasonic sound waves used was 1.7 MHz.

The results are summarized in Table 5.

TABLE 5

| Microorganism (location) | Concentration | | | | | |
|---|---|---|---|---|---|---|
| | 10E1 | 10E2 | 10E3 | 10E4 | 10E5 | 10E6 |
| *B. subtilis* (stairs) | X | X | X | X | X | X |
| *B. subtilis* (ground) | X | X | X | X | X | X |
| *B. subtilis* (above door) | X | X | X | X | 0 | 0 |
| *B. subtilis* (1 m. above outlet of device of invention | X | X | X | X | X | X |
| *B. stearothermophilus* (stairs) | X | X | X | X | X | 0 |
| *B. stearothermophilus* (ground) | X | X | X | X | X | 0 |
| *B. stearothermophilus* (above door) | X | 0 | 0 | 0 | 0 | 0 |
| *B. stearothermophilus* (1 m. above outlet of device of invention | X | X | X | X | X | X |

X: no growth of microorganisms observed;
0: some growth observed

These results clearly demonstrate that using the device and method of the present invention, log 5 reductions were obtained on almost all locations tested, and thus demonstrate the efficacy of the method and device of the invention.

Example 3

Results of European Suspension Test

Using the European Suspension test (described above), the efficacy of method and device of the present invention was tested on eight microorganisms (see below). For each of the microorganisms, two different types of suspensions of the microorganisms were prepared, (1): microorganisms in 0.03% albumin and (2): microorganisms in 0.3% albumin and 0.3% sheep erythrocytes. Ten different locations (L1-L10) were contaminated with both Suspension 1 and Suspension 2 comprising a known amount of each microorganism.

Using the device according to the present invention, the first value of the relative humidity (RH) was determined to be 32.2% at 28.8° C. By vaporizing the disinfectant the relative humidity was increased to 86.3% at 29.1° C., which value was maintained during 255 minutes by vaporizing the disinfectant (4.3 liters) (comprising 5% hydrogen peroxide and 50 ppm silver in water). The disinfecting liquid was vaporized to an average droplet size of 2 μm. The frequency of the ultrasonic sound waves used was 1.7 MHz.

The results are summarized in Table 6:

TABLE 6

| Microorganism | Suspension | Microbicide effect |
|---|---|---|
| Sae DSM 799 | 1 | 6.59 |
| Sae DSM 799 | 2 | 6.63 |
| *A. niger* DSM 1988 | 1 | 5.52 |
| *A. niger* DSM 1988 | 2 | 5.51 |
| *M. terrae* DSM 43227 | 1 | 6.36 |
| *M. terrae* DSM 43227 | 2 | 6.45 |
| *M. avium* DSM 44157 | 1 | 5.41 |
| *M. avium* DSM 44157 | 2 | 5.36 |
| *B. subtilis* ATCC 9372 | 1 | 4.76 |
| *B. subtilis* ATCC 9372 | 2 | 4.79 |
| *E. hirae* DSM 3320 | 1 | 6.97 |
| *E. hirae* DSM 3320 | 2 | 6.81 |
| *P. aeruginosa* DSM 939 | 1 | 5.58 |
| *P. aeruginosa* DSM 939 | 2 | 5.63 |
| *C. albicans* DSM 1386 | 1 | 5.48 |
| *C. albicans* DSM 1386 | 2 | 5.48 |

The results were similar for each of the ten locations tested. These results show that the method and device of the present invention can very effectively be used to reduce or completely eliminate the tested microorganisms.

The invention claimed is:

1. A method for disinfecting a space and the objects present therein, which method comprises at least the following steps of:
 (a) determining a first value of the relative humidity of the air in the space;
 (b) vaporizing a disinfecting liquid comprising hydrogen peroxide at a concentration ranging from 1 to 10 vol. % in the space and thereby increasing the relative humidity to provide a homogenous distribution of the disinfecting liquid in the space until a predetermined second value of the relative humidity of the air in the space is reached; and
 (c) maintaining the relative humidity of the air at the second value for a predetermined time by means of vaporizing the disinfecting liquid,
 wherein the vaporizing of the disinfecting liquid takes place by means of ultrasonic sound waves.

2. The method according to claim 1, wherein vaporizing of the disinfecting liquid takes place by means of ultrasonic sound waves at a frequency of 1.5 MHZ or greater.

3. The method according to claim 2, wherein the frequency ranges from 1.5 MHZ to 2.8 MHz.

4. The method according to claim 1, wherein the second value of the relative humidity is higher than the first value.

5. The method according to claim 4, wherein the second value of relative humidity is 10% or higher than the first value.

6. The method according to claim 1, wherein the disinfecting liquid further comprises silver ions.

7. The method according to claim 1, wherein the disinfecting liquid is vaporized to a droplet size of 10 μm or less.

8. The method according to claim 1, wherein the method is a method of reducing and/or eliminating the amount of micro-organisms in a space or on objects present therein.

9. The method according to claim 8, wherein the micro-organisms comprise gram-positive bacteria, gram-negative bacteria, spore-forming micro-organisms, yeasts, fungi, viruses, mites, or combinations thereof.

10. The method according to claim 9, wherein the disinfecting liquid is vaporized to a droplet size of 3 μm or less.

11. The method according to claim 8, wherein the microorganisms are selected from the group consisting of *Staphylococcus aureus*, MRSA, *Enterococcus faecealis*, *Acinetobacter baumanni*, *Pseudomonas aeruginosa*, *Bacillus subtilis*, *Bacillus staerothermophilus*, *Aespirgillus niger*, *Mycobacterium terrae*, *Mycobacterium avium*, *Enterococcus hirae Candida albicans* and *Dermatophagoides pteronyssinus*.

12. The method according to claim 1, wherein the vaporizing of the disinfecting liquid is performed using a device comprising one or a plurality of ceramic elements.

13. The method according to claim 1, further comprising using an indicator positioned outside the space to determine whether the disinfecting liquid is being vaporized.

\* \* \* \* \*